United States Patent
Tang et al.

(10) Patent No.: US 11,427,569 B2
(45) Date of Patent: Aug. 30, 2022

(54) BENZOIMIDAZOLE INDOLYL METHANES AND METHODS OF USING THEM TO INHIBIT PCKS9 AND PCKS9-MEDIATED AILMENTS

(71) Applicant: Wisconsin Alumni Research Foundation, Madison, WI (US)

(72) Inventors: Weiping Tang, Middleton, WI (US); Gabrielle N. Winston-McPherson, Seattle, WA (US); Haibo Xie, Madison, WI (US); Alan D. Attie, Madison, WI (US); Mark Patrick Keller, McFarland, WI (US); Ka Yang, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 134 days.

(21) Appl. No.: 16/789,887

(22) Filed: Feb. 13, 2020

(65) Prior Publication Data
US 2020/0262819 A1  Aug. 20, 2020

Related U.S. Application Data

(60) Provisional application No. 62/806,019, filed on Feb. 15, 2019.

(51) Int. Cl.
| | | |
|---|---|---|
| *C07D 403/06* | (2006.01) | |
| *C07D 401/14* | (2006.01) | |
| *C07D 409/06* | (2006.01) | |
| *C07D 413/14* | (2006.01) | |

(52) U.S. Cl.
CPC ......... *C07D 403/06* (2013.01); *C07D 401/14* (2013.01); *C07D 409/06* (2013.01); *C07D 413/14* (2013.01); *C07B 2200/05* (2013.01)

(58) Field of Classification Search
CPC ... C07D 401/14; C07D 403/06; C07D 413/14
See application file for complete search history.

(56) References Cited

U.S. PATENT DOCUMENTS 6,541,486 B1 * 4/2003 Bitler ................... C07D 235/16
514/303

OTHER PUBLICATIONS

Mukhopadhyay et al. RSC Advances, 2011, 1, 1033-1037.*
Cao, A., Wu, M., Li, H., and Liu, J., "Janus Kinase activation by cytokine oncostatin M decreases PCSK9 expression in liver cells," *J Lipid Res* 52, 518-530, (2011).
Crunkhorn, S. "Trial watch: PCSK9 antibody reduces LDL cholesterol," *Nat Rev Drug Discov* 11, 11, (2012).
Horton, J. D., Cohen, J.C., and Hobbs, H. H., "PCSK9: a convertase that coordinates LDL catabolism," *J. Lipid Res*. 50 Suppl, S172-177, (2009).
Li, H., Dong, B., Park, S. W., Lee, H. S., Chen, W., and Liu, J., "Hepatocyte nuclear factor 1alpha plays a critical role in PCSK9 gene transcription and regulation by the natural hypocholesterolemic compound berberine," *J Biol Chem* 284, 28885-28895, (2009).
Vogel, R. A., "PCSK9 inhibition: the next statin," *J Am Coll Cardiol* 59, 2354-2355, (2012).

* cited by examiner

*Primary Examiner* — Paul V Ward
(74) *Attorney, Agent, or Firm* — Joseph T. Leone; DeWitt LLP

(57) ABSTRACT

Described are benzoimidazole indolyl methane compounds, pharmaceutical compositions containing them, and use of the compounds to inhibit PCSK9-mediated ailments. The compounds have the structure:

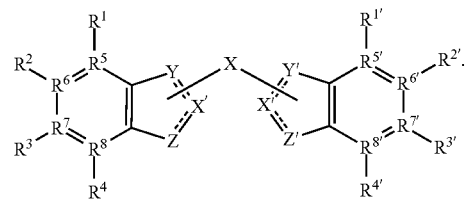

11 Claims, 4 Drawing Sheets

BENZOIMIDAZOLE INDOLYL METHANES AND METHODS OF USING THEM TO INHIBIT PCKS9 AND PCKS9-MEDIATED AILMENTS

FEDERAL FUNDING STATEMENT

This invention was made with government support under GM088285 awarded by the National Institutes of Health. The government has certain rights in the invention.

CROSS-REFERENCE TO RELATED APPLICATIONS

Prior is hereby claimed to provisional application Ser. No. 62/806,019, filed Feb. 15, 2019, which is incorporated herein by reference.

BACKGROUND

Proprotein convertase subtilisin kexin type 9 (PCSK9) belongs to the proteinase K subfamily of secretory proteases. This protein plays a major regulatory role in cholesterol homeostasis. PCSK9 regulates plasma LDL-cholesterol (LDL-C) levels by directing LDL receptor (LDLR) to lysosomal degradation, resulting in reduced LDL clearance and accumulation of LDL in the circulation. Gain of function mutations of PCSK9 lead to hyperlipidemia0 and premature coronary artery disease (CAD) in humans, whereas loss of function mutations of PCSK9 are associated with lower levels of LDL and protection from CAD.

PCSK9 expression is actively regulated at transcription levels. Statins are known to stimulate PCSK9 transcription which in turn curbs the efficacy of statins in LDL lowering in humans. A few other molecules including berberine and oncostatin have been shown to suppress PCSK9 transcription which in turn contributes to the hypolipidemic effects of these agents. The PCSK9 phenotypic assay is designed to identify compounds that destabilize PCSK9 in human hepatoma cell lines (HepG2). See, for example, Horton, J. D., Cohen, J. C., and Hobbs, H. H., "PCSK9: a convertase that coordinates LDL catabolism," *J. Lipid Res.* 50 Suppl, S172-177, (2009); Crunkhorn, S. "Trial watch: PCSK9 antibody reduces LDL cholesterol," *Nat Rev Drug Discov* 11, 11, (2012); Vogel, R. A., "PCSK9 inhibition: the next statin," *J Am Coll Cardiol* 59, 2354-2355, (2012); Li, H., Dong, B., Park, S. W., Lee, H. S., Chen, W., and Liu, J., "Hepatocyte nuclear factor 1alpha plays a critical role in PCSK9 gene transcription and regulation by the natural hypocholesterolemic compound berberine," *J Biol Chem* 284, 28885-28895, (2009); and Cao, A., Wu, M., Li, H., and Liu, J., "Janus Kinase activation by cytokine oncostatin M decreases PCSK9 expression in liver cells," *J Lipid Res* 52, 518-530, (2011).

SUMMARY

Disclosed herein is a compound having a structure as shown in Formula I:

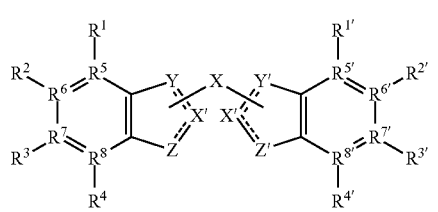
(Formula I)

wherein

X is selected from —$CH_2$—, —$CD_2$—, —$CF_2$—, —CHF—, —CH(OH)—, —C(=O)—, —N(R)(R)—, —S—, —S(=O)—, —S(=O)$_2$—, or cyclopropylenyl

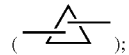

X', Y, Y', Z, and Z' are independently selected from —CH—, —C(R)—, —C(=O)—, —NH—, —N(R)—, —O—, or —S—;

each R is independently selected from hydrogen, halogen, alkyl, and aryl;

$R^1$, $R^2$, $R^3$, $R^4$, $R^{1'}$, $R^{2'}$, $R^{3'}$, and $R^{4'}$ are selected from hydrogen, halogen, alkyl, or aryl, provided that not all of $R^1$, $R^2$, $R^3$, $R^4$, $R^{1'}$, $R^{2'}$, $R^{3'}$, and $R^{4'}$ are simultaneously hydrogen;

$R^5$, $R^6$, $R^7$, $R^8$, $R^{5'}$, $R^{6'}$, $R^{7'}$ and $R^{8'}$ are independently selected from —C— or —N—, provided that not more than two of $R^5$, $R^6$, $R^7$, $R^8$ and not more than two of $R^{5'}$, $R^{6'}$, $R^{7'}$ and $R^{8'}$ are simultaneously -N—; and salts thereof.

Falling within the definition of compounds of Formula I, also specifically disclosed herein are compounds having a structure as shown in Formula II, III, or IV:

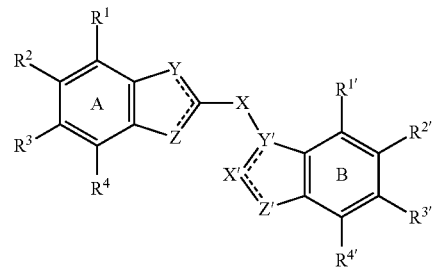
(Formula II)

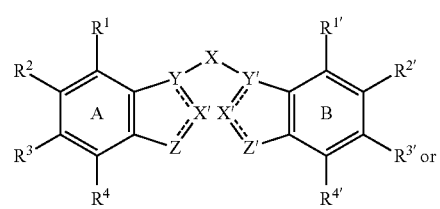
(Formula III)

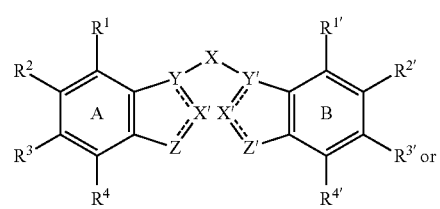
(Formula IV)

The various substituents in Formulas II, III, and IV are the same as described previously for Formula I compounds.

Specifically disclosed herein are the following compounds:

(HX178)

(HX179)

(HX181)

(HX182)

(HX81)

(HX183)

(HX184)

(HX185)

(HX186)

(9577)

-continued
(HX257)
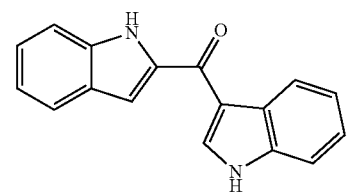 [SMILES: O=C(c1cc2ccccc2[nH]1)c1c[nH]c2ccccc12]
(HX258)
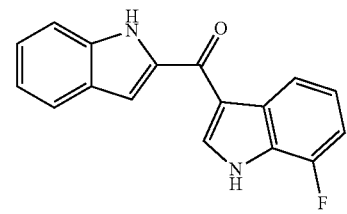 [SMILES: O=C(c1cc2ccccc2[nH]1)c1c[nH]c2c(F)cccc12]
(HX259)
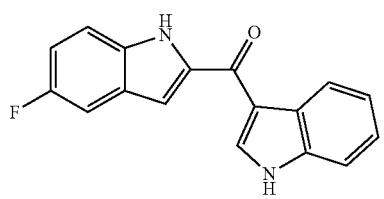
(HX240)
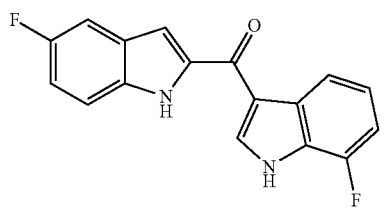
(HX262)
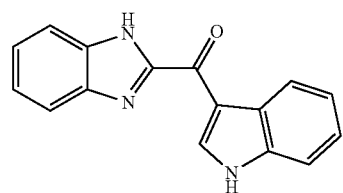
(MF025)
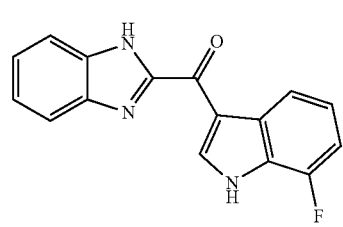
(HX235)
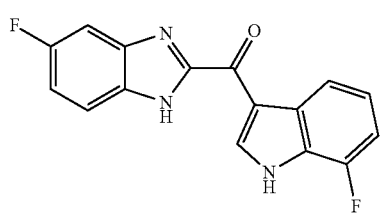
-continued
(HX261)
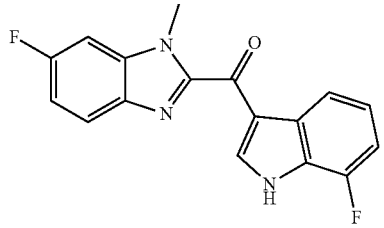
(HX2-123)
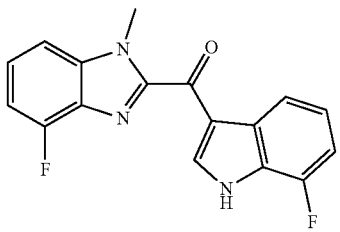
(HX212)
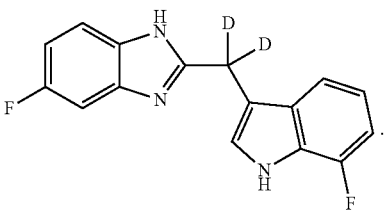
(HX2-138)
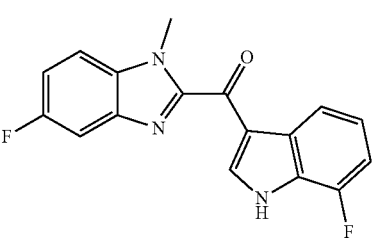
(HX2-139)
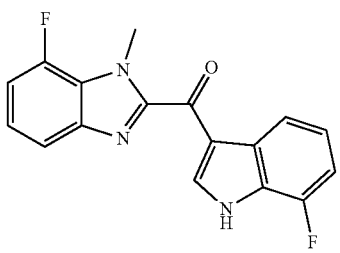
(HX271)
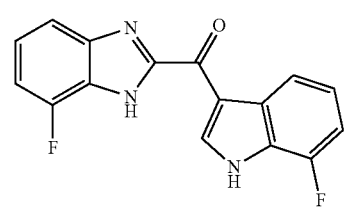

(HX2-080)
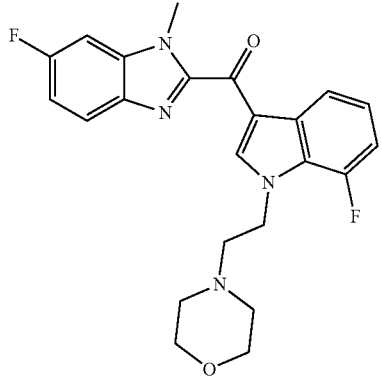
Additional compounds disclosed herein include:
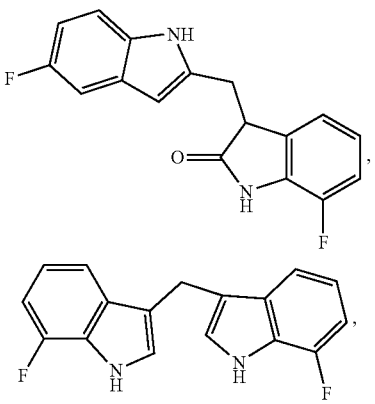
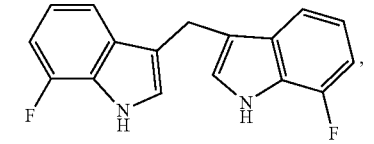
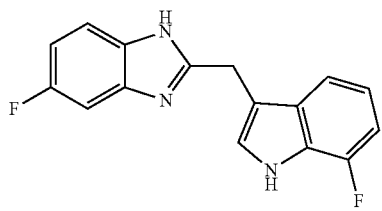
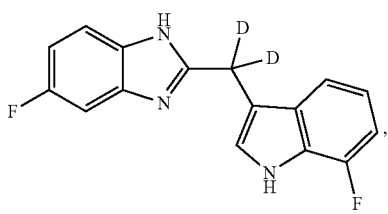
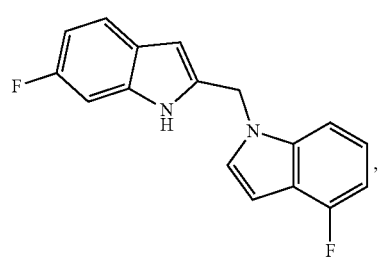
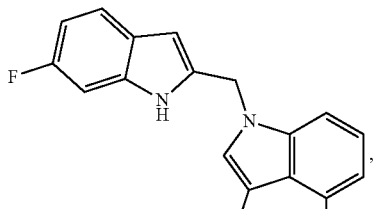
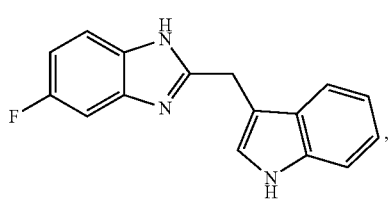
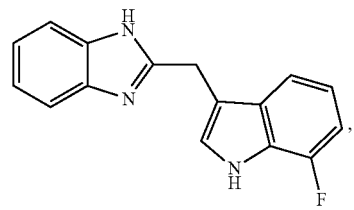
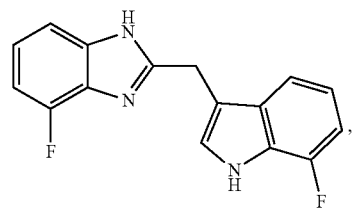
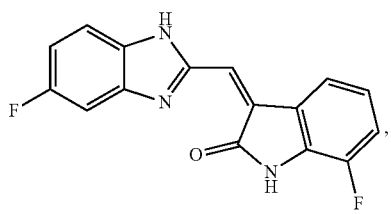
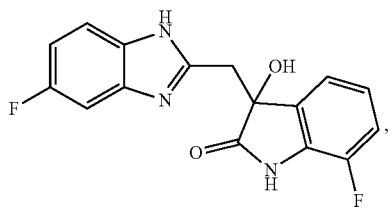
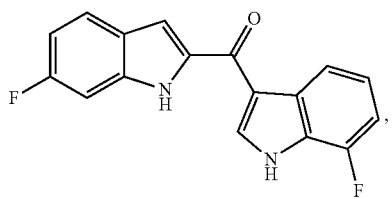
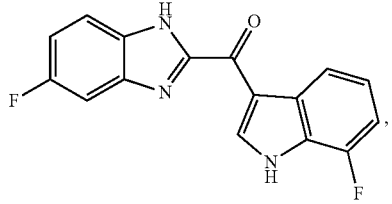

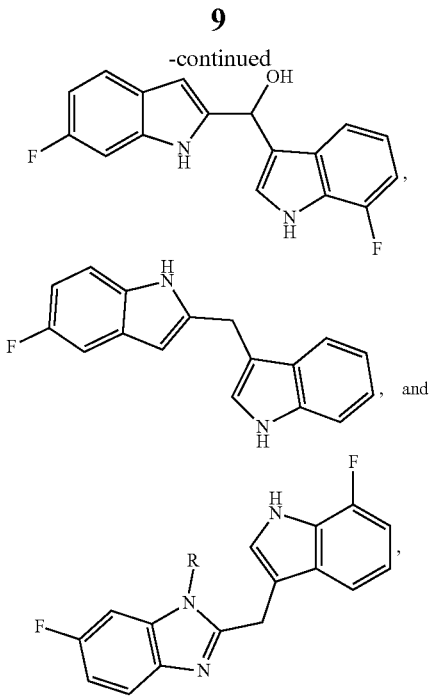

wherein R is selected from $C_1$-$C_6$-linear or branched alkyl, Ph, —$C_1$-$C_6$-Ph, —$C_1$-$C_6$-(4-pyridine), —$C_1$-$C_6$-(3-pyridine), and —$C_1$-$C_6$—OH.

Also disclosed herein is a pharmaceutical composition for ameliorating a PCSK9-mediated ailment, the composition comprising a PCSK9-inhibitory amount of a compound as recited in above in combination with a pharmaceutically suitable carrier.

Additionally disclosed herein is a method of inhibiting PCSK9-mediated ailments in mammals, including humans, the method comprising administering to a mammal a PCSK9-inhibitory amount of a compound as recited hereinabove.

DETAILED DESCRIPTION

Definitions

Figure 1:
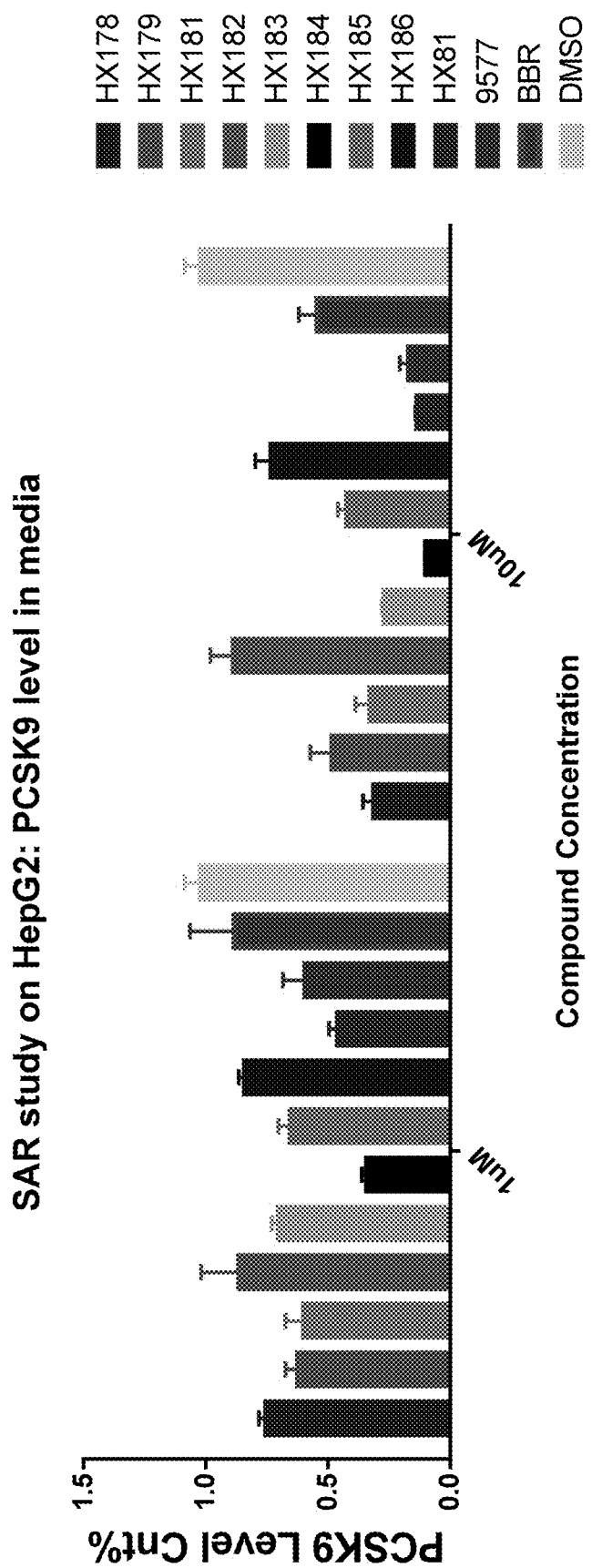
FIG. 1 is a histogram depicting PCSK9-inhibitory activity of selected compounds according to the present disclosure in HepG2 cells (a human liver cancer cell line, ATCC HB-8065, at 1 μM concentration (left-hand bars) and at 10 μM centration (right-hand bars). See the Examples for complete experimental details.
Figure 2A:
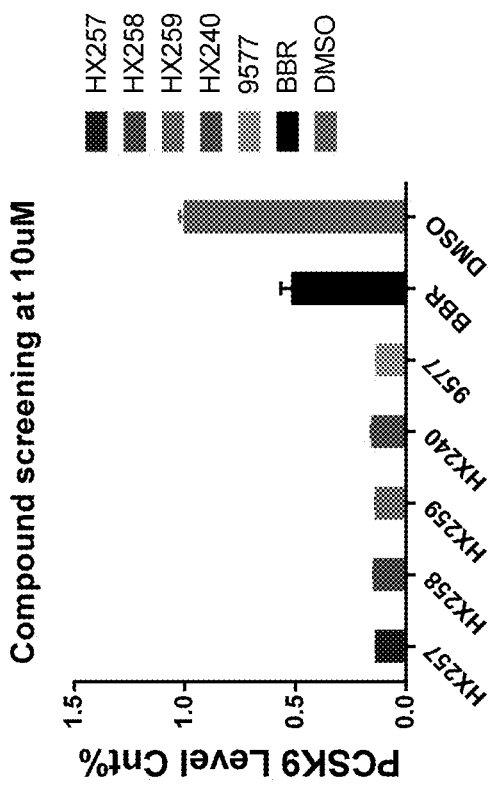
FIG. 2A is a histogram depicting PCSK9-inhibitory activity of another set of selected compounds according to the present disclosure in HepG2 cells at 1 μM concentration.
Figure 2B:
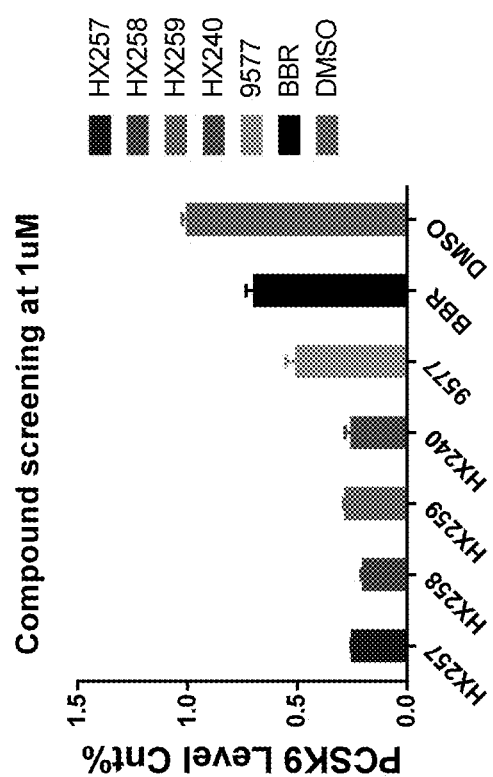
FIG. 2B is a histogram depicting PCSK9-inhibitory activity of the same compounds as for FIG. 2A, but at 10 μM concentration.
Figures 3A, 3B:
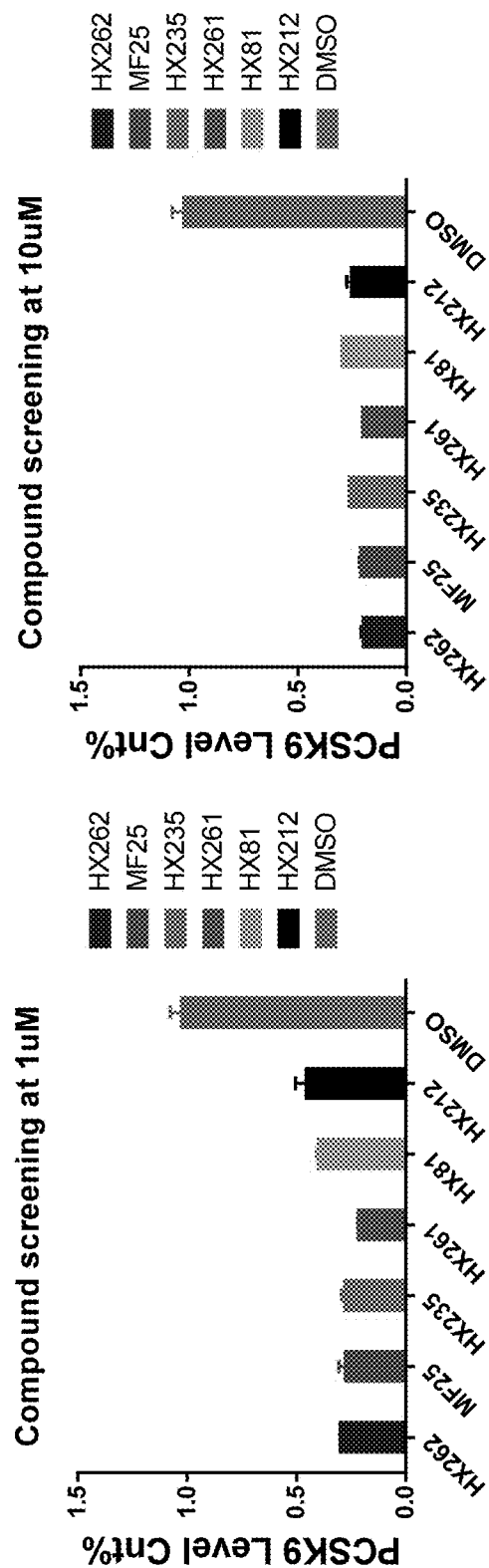
FIG. 3A is a histogram depicting PCSK9-inhibitory activity of another set of selected compounds according to the present disclosure in HepG2 cells at 1 μM concentration.
FIG. 3B is a histogram depicting PCSK9-inhibitory activity of the same compounds as for FIG. 3A, but at 10 μM concentration.
Figure 4:
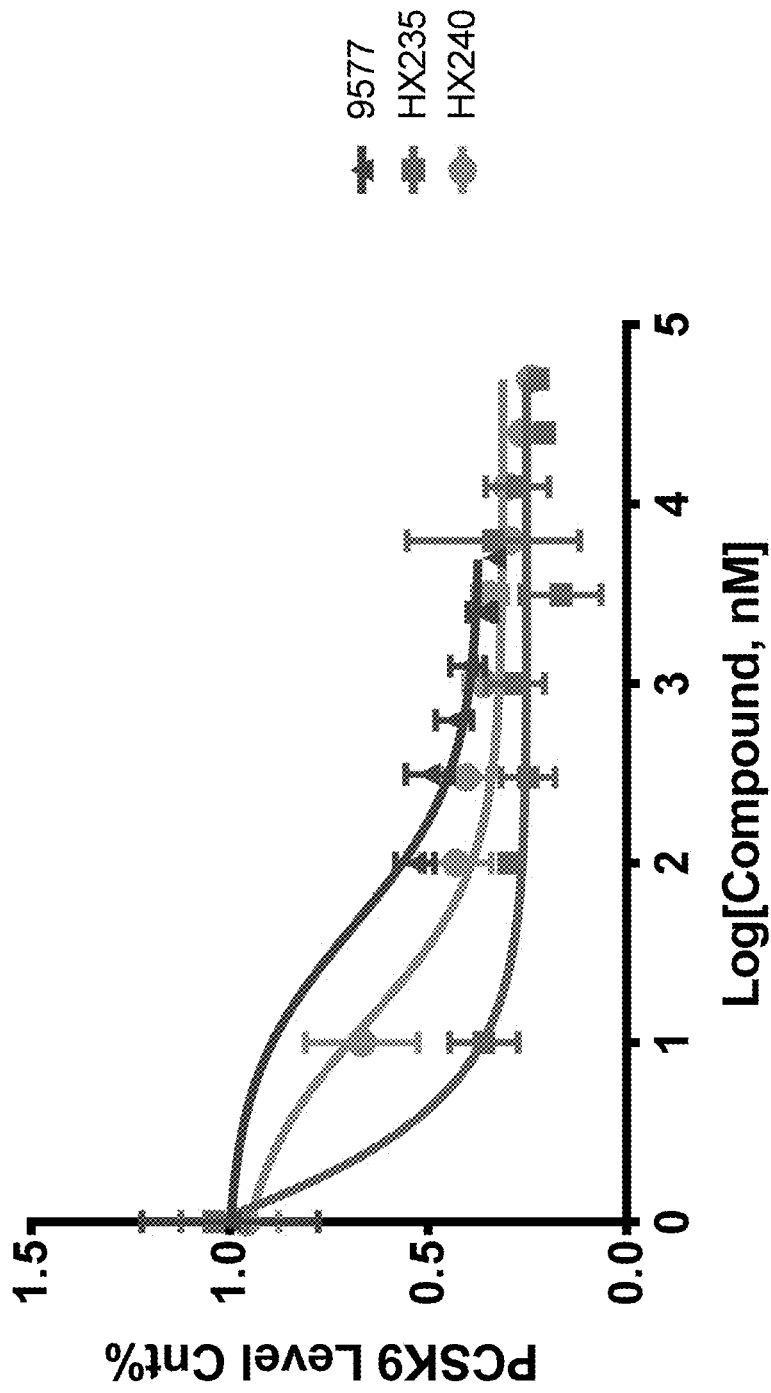
FIG. 4 is a graph depicting dose-response curves for extracellular PCSK9 concentrations in cultured Hep2G cells for the compounds 9577, HX235, and HX240.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made. That is, unless specifically stated to the contrary, "a" and "an" mean "one or more." The phrase "one or more" is readily understood by one of skill in the art, particularly when read in context of its usage. For example, "one or more" substituents on a phenyl ring designates one to five substituents.

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the method described herein, as well as any additional or optional ingredients, components, or limitations described herein or otherwise useful in synthetic organic chemistry.

The term "contacting" refers to the act of touching, making contact, or of bringing to immediate or close proximity, including at the molecular level, for example, to bring about a chemical reaction, or a physical change, e.g., in a solution or in a reaction mixture.

An "effective amount" refers to an amount of a chemical or reagent effective to facilitate a chemical reaction between two or more reaction components, and/or to bring about a recited effect. Thus, an "effective amount" generally means an amount that provides the desired effect.

The term "solvent" refers to any liquid that can dissolve a compound to form a solution. Solvents include water and various organic solvents, such as hydrocarbon solvents, for example, alkanes and aryl solvents, as well as halo-alkane solvents. Examples include hexanes, benzene, toluene, xylenes, chloroform, methylene chloride, dichloroethane, and alcoholic solvents such as methanol, ethanol, propanol, isopropanol, and linear or branched (sec or tert) butanol, and the like. Aprotic solvents that can be used in the method include, but are not limited to perfluorohexane, α,α,α-trifluorotoluene, pentane, hexane, cyclohexane, methylcyclohexane, decalin, dioxane, carbon tetrachloride, freon-11, benzene, toluene, triethyl amine, carbon disulfide, diisopropyl ether, diethyl ether, t-butyl methyl ether (MTBE), chloroform, ethyl acetate, 1,2-dimethoxyethane (glyme), 2-methoxyethyl ether (diglyme), tetrahydrofuran (THF), methylene chloride, pyridine, 2-butanone (MEK), acetone, hexamethylphosphoramide, N-methylpyrrolidinone (NMP), nitromethane, dimethylformamide (DMF), acetonitrile, sulfolane, dimethyl sulfoxide (DMSO), propylene carbonate, and the like.

The term "alkyl" refers to a branched or unbranched carbon chain having, for example, about 1-20 carbon atoms, and often 1-12, 1-10, 1-8, 1-6, or 1-4 carbons. Examples include, but are not limited to, methyl, ethyl, 1-propyl, 2-propyl, 1-butyl, 2-methyl-1-propyl, 2-butyl, 2-methyl-2-propyl(t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. The alkyl can also be optionally partially or fully unsaturated in certain embodiments. As such, the recitation of an alkyl group optionally includes both alkenyl and alkynyl groups. The alkyl can be a monovalent hydrocarbon radical, as described and exemplified above, or it can be a divalent hydrocarbon radical (i.e., an alkylene). In some embodiments, certain alkyl groups can be excluded from a definition. For example, in some embodiments, methyl, ethyl, propyl, butyl, or a combination thereof, can be excluded from a specific definition of alkyl in an embodiment.

The term "cycloalkyl" refers to cyclic alkyl groups of, for example, 3 to about 12, 3 to about 10, 3 to about 8, about 4 to about 8, or 5-6, carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

As used herein, "aryl" refers to an aromatic hydrocarbon group derived from the removal of one hydrogen atom from a single carbon atom of a parent aromatic ring system. The radical attachment site can be at a saturated or unsaturated carbon atom of the parent ring system. The aryl group can have from 6 to about 20 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

The term "heteroaryl" refers to a monocyclic, bicyclic, or tricyclic ring system containing one, two, or three aromatic rings and containing at least one nitrogen, oxygen, or sulfur atom in an aromatic ring, and that can be unsubstituted or substituted, for example, with one or more, and in particular one to three, substituents, as described in the definition of "substituted". Typical heteroaryl groups contain 2-20 carbon atoms in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, (β-carbolinyl, carbazolyl, chromenyl, cinnolinyl, dibenzo[b,d]furanyl, furazanyl, furyl, imidazolyl, imidizolyl, indazolinyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or —(C1-C6)alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, silicon, and sulfur, and optionally substituted with one or more groups as defined for the term "substituted". A heterocycle can be a monocyclic, bicyclic, or tricyclic group. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholinyl, piperazinyl, piperidinyl, pyrazolidinyl, pyrazolinyl, pyrrolidine, pyrroline, quinuclidine, tetrahydrofuranyl, and thiomorpholine, where the point of attachment can be at any atom accessible by known synthetic methods.

The term "substituted" indicates that one or more hydrogen atoms on the group indicated in the expression using "substituted" is replaced with a "substituent". The number referred to by 'one or more' can be apparent from the moiety one which the substituents reside. For example, one or more can refer to, e.g., 1, 2, 3, 4, 5, or 6; in some embodiments 1, 2, or 3; and in other embodiments 1 or 2. The substituent can be one of a selection of indicated groups, or it can be a suitable group known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, amino, alkylamino, dialkylamino, trifluoromethyl, trifluoromethoxy, trifluoromethylthio, difluoromethyl, acylamino, nitro, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl(alkyl)amine, and cyano. Additionally, suitable substituent groups can be, e.g., —X, —R, —O—, —OR, —SR, —S—, —NR$_2$, —NR$_3$, =NR, —CX$_3$, —CN, —OCN, —SCN, —N=C=O, —NCS, —NO, —NO2, =N$_2$, —N$_3$, —NC(=O)R, —C(=O)R, —C(=O)NRR, —S(=O)$_2$O—, —S(=O)$_2$OH, —S(=O)$_2$R, —OS(=O)$_2$OR, —S(=O)$_2$NR, —S(=O)R, —OP(=O)O$_2$RR, —P(=O)O$_2$RR, —P(=O)(O—)$_2$, —P(=O)(OH)$_2$, —C(=O)R, —C(=O)X, —C(S)R, —C(O)OR, —C(O)O—, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above are excluded from the group of potential values for substituents on the substituted group.

A protecting group is any chemical moiety capable of selective addition to and removal from a reactive site to allow manipulation of a chemical entity at sites other than the reactive site. Many protecting groups are known in the art. A large number of protecting groups and corresponding chemical cleavage reactions are described in "Protective Groups in Organic Synthesis," Theodora W. Greene (John Wiley & Sons, Inc., New York, 1991, ISBN 0-471-62301-6) ("Greene", which is incorporated herein by reference). See also the 5$^{th}$ edition of this same work, published under the title "Greene's Protective Groups in Organic Synthesis," ISBN-13: 978-1118057483, ©2014, John Wiley & Sons, Inc. Greene describes many nitrogen protecting groups, for example, amide-forming groups. In particular, see Chapter 1, Protecting Groups: An Overview, Chapter 2, Hydroxyl Protecting Groups, Chapter 4, Carboxyl Protecting Groups, and Chapter 5, Carbonyl Protecting Groups. For additional information on protecting groups, see also Kocienski, Philip J. "Protecting Groups," (Georg Thieme Verlag Stuttgart, New York, 1994), which is incorporated herein by reference. Typical nitrogen protecting groups described in Greene include benzyl ethers, silyl ethers, esters including sulfonic acid esters, carbonates, sulfates, and sulfonates. For example, suitable nitrogen protecting groups include substituted methyl ethers; substituted ethyl ethers; p-chlorophenyl, p-methoxyphenyl, 2,4-dinitrophenyl, benzyl; substituted benzyl ethers (p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, diphenylmethyl, 5-dibenzosuberyl, triphenylmethyl, p-methoxyphenyl-diphenylmethyl, di(p-methoxyphenyl)phenylmethyl, tri(p-methoxyphenyl)methyl, 1,3-benzodithiolan-2-yl, benzisothiazolyl S,S-dioxido); silyl ethers (silyloxy groups) (trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, t-butylmethoxy-phenylsilyl); esters (formate, benzoylformate, acetate, choroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), pivaloate, adamantoate, crotonate, 4-methoxycrotonate, benzoate, p-phenylbenzoate, 2,4,6-trimethylbenzoate(mesitoate)); carbonates(methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, methyl dithiocarbonate); groups with assisted cleavage (2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, miscellaneous esters (2,6-dichloro-4-methylphenoxyacetate, 2,6-dichloro-4-(1,1,3,3 tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate (tigloate), o-(methoxycarbonyl)benzoate, p-poly-benzoate, α-naphthoate, nitrate, alkyl N,N,N',N'-tetramethyl-phosphorodiamidate, n-phenylcarbamate, borate, 2,4-dinitrophenylsulfenate); or sulfonates (methanesulfonate(mesylate), benzenesulfonate, benzylsulfonate, tosylate, or triflate).

The more common of the amine-protecting groups have trivial abbreviations that are widely used in the literature and include: carbobenzyloxy (Cbz) group (removed by hydrogenolysis), p-methoxybenzyl carbonyl(Moz or MeOZ) group (removed by hydrogenolysis), tert-butyloxycarbonyl (BOC) group (common in solid phase peptide synthesis; removed by concentrated strong acid (such as HCl or CF$_3$COOH), or by heating to >80° C., 9-fluorenylmethyloxycarbonyl (FMOC) group (also common in solid phase peptide synthesis; removed by base, such as piperidine), acetyl (Ac) group (removed by treatment with a base), benzoyl (Bz) group (removed by treatment with a base), benzyl (Bn) group (removed by hydrogenolysis), carbamate group (removed by acid and mild heating), p-methoxybenzyl (PMB) (removed by hydrogenolysis), 3,4-dimethoxybenzyl (DMPM) (removed by hydrogenolysis), p-methoxyphenyl (PMP) group (removed by ammonium cerium(IV) nitrate (CAN)), tosyl (Ts) group (removed by concentrated acid and strong reducing agents), sulfonamide groups (Nosyl & Nps; removed by samarium iodide, tributyltin hydride).

A "pharmaceutically-suitable salt" is any acid or base addition salt whose counter-ions are non toxic to a patient (including a veterinary patient) in pharmaceutical doses of the salts, so that the beneficial pharmacological effects inherent in the free base or free acid are not vitiated by side effects ascribable to the counter-ions. A host of pharmaceutically-suitable salts are well known in the art. For basic active ingredients, all acid addition salts are useful as sources of the free base form even if the particular salt, per se, is desired only as an intermediate product as, for example, when the salt is formed only for purposes of purification, and identification, or when it is used as intermediate in preparing a pharmaceutically-suitable salt by ion exchange procedures. Pharmaceutically-suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene bis-b-hydroxynaphthoates, gentisates, isethionates, di-p-toluoyltartrates, methane sulphonates, ethanesulphonates, benzenesulphonates, p-toluenesulphonates, cyclohexylsulphamates, quinates, and the like. Base addition salts include those derived from alkali or alkaline earth metal bases or conventional organic bases, such as triethylamine, pyridine, piperidine, morpholine, N methylmorpholine, and the like.

The Compounds:

Disclosed herein is a family of structurally related benzoimidazole indolyl methane compounds. The compounds include various substituted benzoimidazole indolyl methanes, as well as analogous benzoimidazole indolyl methane ketones and diindolyl methane ketones. Also disclosed herein is a method of using these compounds to inhibit and/or amelioriate proprotein convertase subtilisin/kexin type 9 (PCSK9)-mediated ailments, such as coronary heart disease, hypercholesterolemia and/or hyperlipidemia. Also disclosed herein are pharmaceutical compositions that contain a pharmaceutically effective amount of one or more of the benzoimidazole indolyl methane compounds disclosed herein.

Synthesis of the Compounds:

The synthesis of the compounds is best illustrated by an example. All of the remaining compounds disclosed herein can be fabricated using similar reaction schemes and the appropriate starting materials. The overall synthesis for compound HX81 is as follows:

Reaction Scheme 1

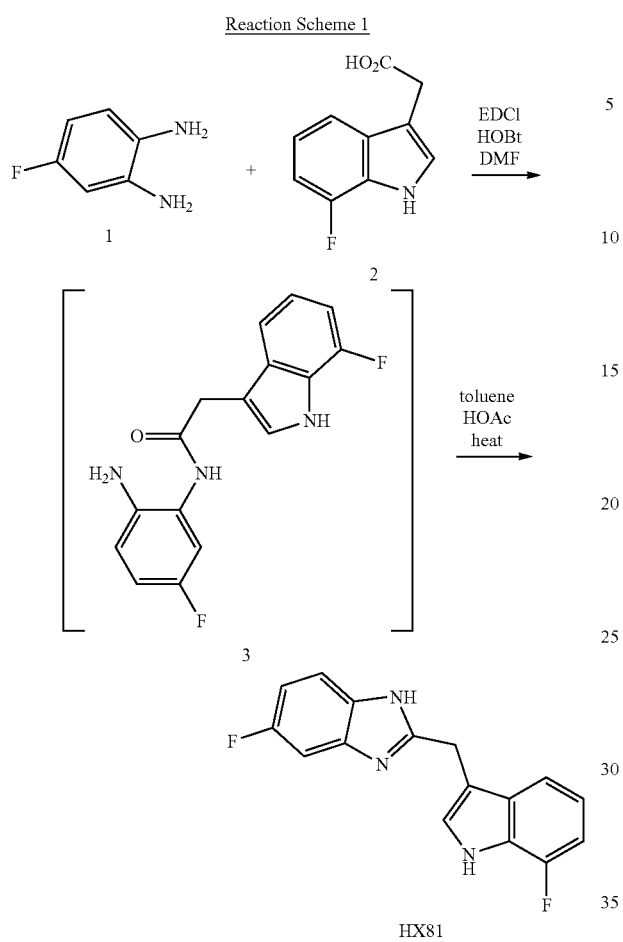

The step-by-step procedures for the synthesis of compound HX81 proceeds as follows:

Reaction Scheme 2

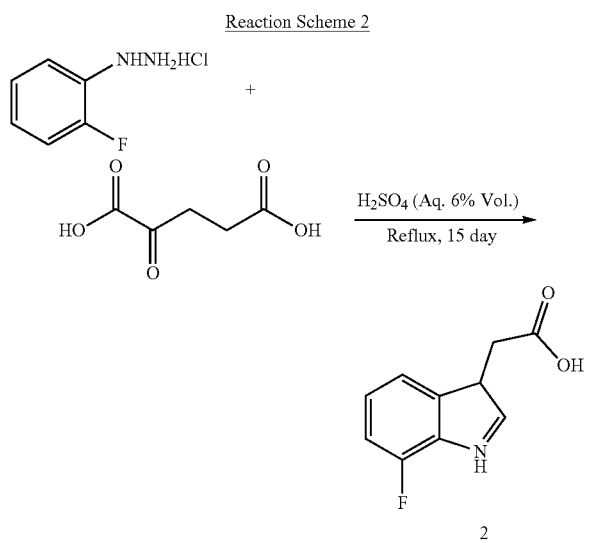

A 500 mL, two-necked, round-bottomed flask is fitted with a mechanical stirrer and a reflux condenser. A solution of 12 mL sulfuric acid in 200 mL of water is introduced into the flask, followed by 8.13 g (50 mmol) of 2-fluorophenyl-hydrazine hydrochloride and 7.3 g (50 mmol) of α-ketoglutaric acid. The resulting mixture is warmed to reflux for 15 days. After cooling to room temperature, the reaction mixture is extracted with 300 mL of ethyl acetate, washed with three 100 mL portions of hydrochloric acid (2.0 M), and dried over sodium sulfate. The solvents are removed on a rotary evaporator. The residue was then purified by silica gel column chromatography, yielding 3.1 g (31%) of solid. $^1$H NMR (400 Mz, DMSO, TMS): δ 11.40 (s, 1H), 7.35-7.27 (m, 2H), 6.99-6.86 (m, 2H), 3.65 (s, 2H).

Reaction Scheme 3

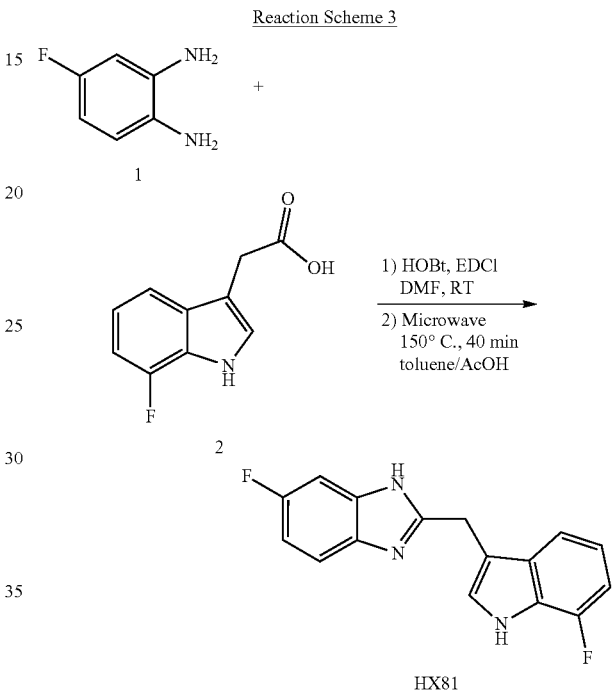

A 25 mL, round-bottomed flask is fitted with a mechanical stirrer. A solution of 1.1 g (5.64 mmol) of 7-fluoroindole-3-acetic acid, 0.862 g (6.83 mmol) of 1,2-diamino-4-fluorobenzene, and 0.864 g (5.64 mmol) of hydroxybenzotriazole in 10 mL of dimethylformamide is introduced into the flask, followed by 1.406 g (7.33 mmol) of N-ethyl-N'-(3-dimethylaminopropyl)carbodiimide hydrochloride. After stirring for 4 h, the reaction mixture is diluted by 150 mL ethyl acetate, washed with three 100 mL portions of water, and dried over sodium sulfate. The solvents were removed on a rotary evaporator. The residue was suspended in 6 mL of toluene and 3 mL of acetic acid and irradiated by microwave hold on at 130° C. for 30 min. The reaction mixture was concentrated by a rotary evaporator. The residue was then purified by silica gel column chromatography, yielding 1.4 g (88%) of solid compound HX81: $^1$H NMR (400 MHz, DMSO, TMS) δ 12.19 (s, 1H), 11.47 (s, 1H), 7.56-7.12 (m, 4H), 7.00-6.84 (m, 3H), 4.27 (s, 2H). HRMS (ESI) m/z calc'd. For $C_{16}H_{11}F_2N_3$ (M+H), 284.0994 found 284.0995.

The biological activity of compound HX81 for reducing the amount PCSK9 protein in medium and inside the cells:
IC50 in medium: 1.4 to 40 nM
IC50 inside the cells: 3 to 32 nM
See below for experimental details.

Using the above-noted synthesis, compounds having a structure as shown in Formula I can be fabricated:

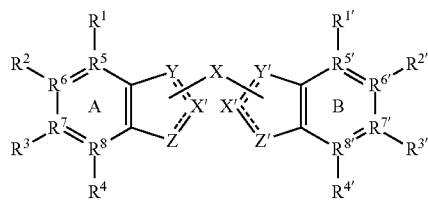
(Formula I)

wherein
X is selected from —CH$_2$—, —CD$_2$—, —CF$_2$—, —CHF—, —CH(OH)—, —C(=O)—, —N(R)(R)—, —S—, —S(=O)—, —S(=O)$_2$—, or cyclopropylene

;

X', Y, Y', Z, and Z' are independently selected from —CH—, —C(R)—, —C(=O)—, —NH—, —N(R)—, —O—, or —S—;
each R is independently selected from hydrogen, halogen, alkyl, aryl;
R$^1$, R$^2$, R$^3$, R$^4$, R$^{1'}$, R$^{2'}$, R$^{3'}$, and R$^{4'}$ are selected from hydrogen, halogen, alkyl, or aryl, provided that not all of R$^1$, R$^2$, R$^3$, R$^4$, R$^{1'}$, R$^{2'}$, R$^{3'}$, and R$^{4'}$ are simultaneously hydrogen;
R$^5$, R$^6$, R$^7$, R$^8$, R$^{5'}$, R$^{6'}$, R$^{7'}$ and R$^{8'}$ are independently selected from —C— or —N—, provided that not more than two of R$^5$, R$^6$, R$^7$, R$^8$ and not more than two of R$^{5'}$, R$^{6'}$, R$^{7'}$ and R$^{8'}$ are simultaneously -N—; and
salts thereof.

The rings A or B can be nitrogen containing heterocycles. Thus, in combination with the fused X', Y, Z, Y', and Z' substituents, the two fused ring structures may be, by way of example and not limitation:

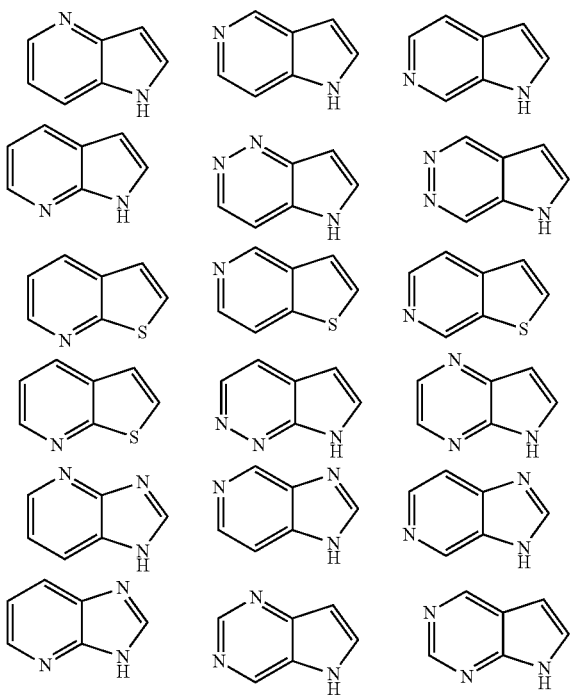

-continued

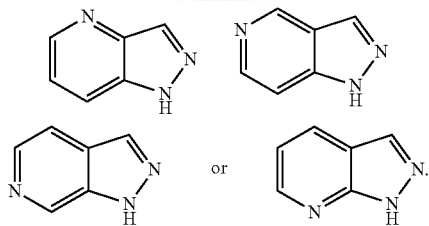

The rings A and B may also contain only carbon atoms in the ring. Thus, the compounds disclosed herein also include:

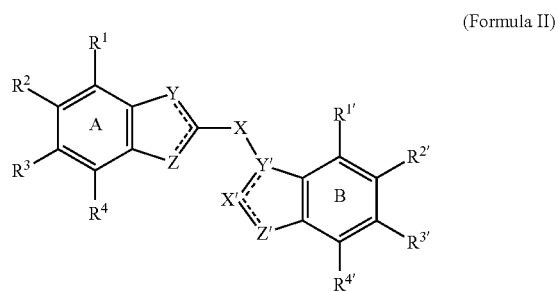
(Formula II)

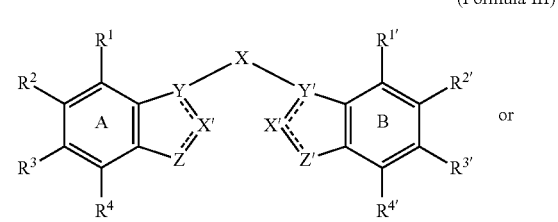
(Formula III)
or

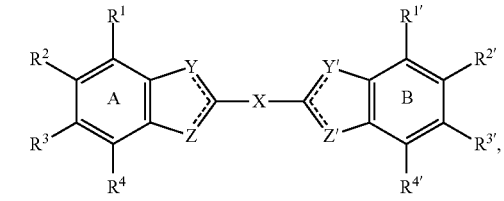
(Formula IV)

wherein all of the substituents are as described previously.

Specifically disclosed herein are the following compounds:

Benzoimidazole indolyl methanes (BIIMs):

HX178

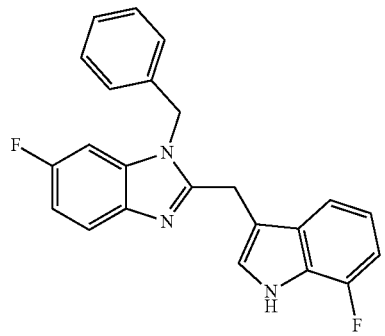

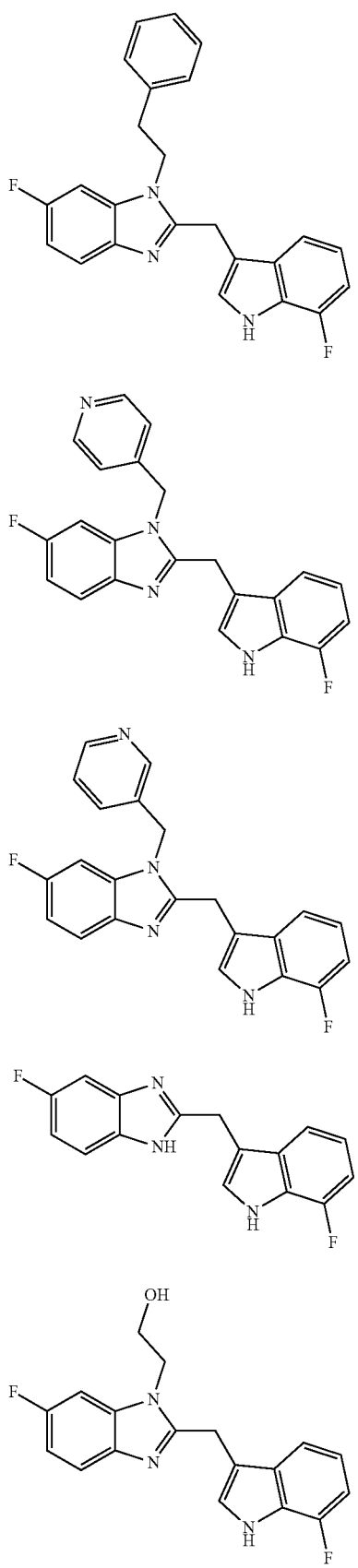
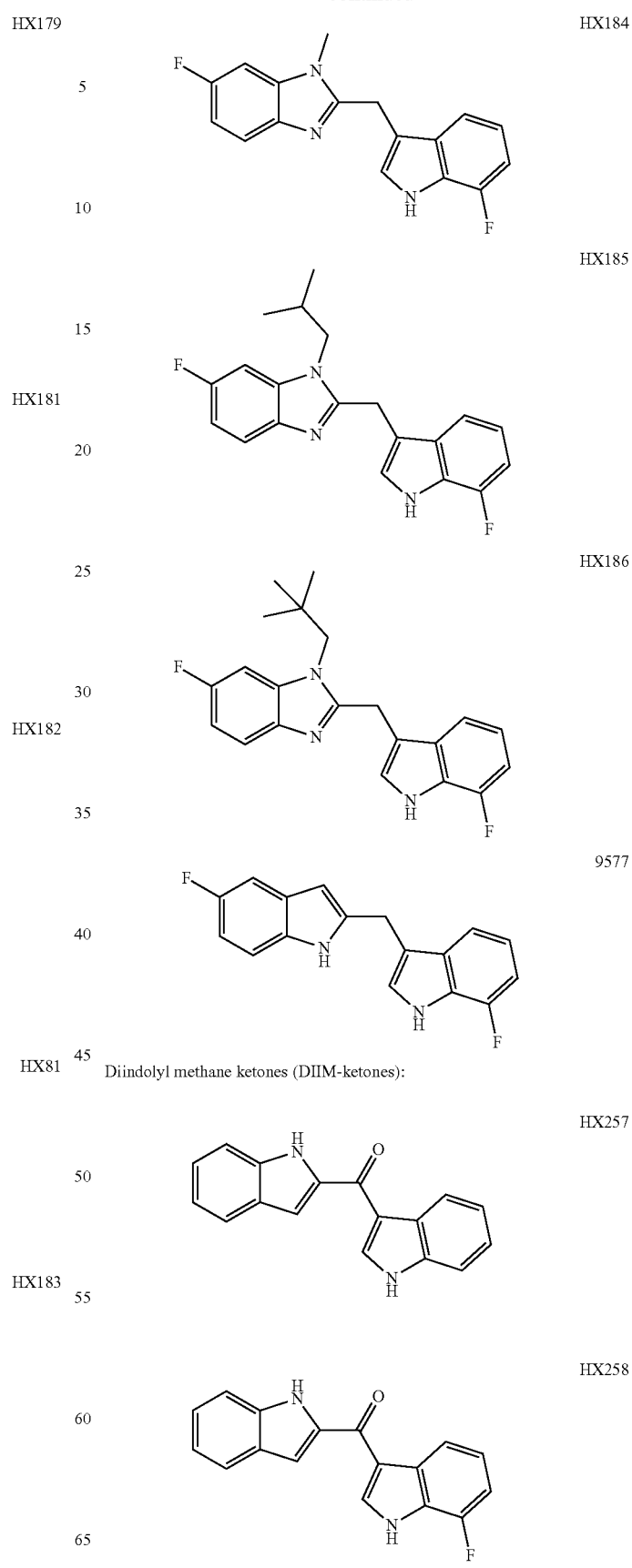
Diindolyl methane ketones (DIIM-ketones):

-continued

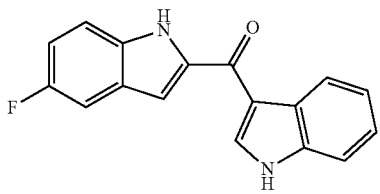 [SMILES: O=C(c1cc2cc(F)ccc2[nH]1)c1c[nH]c2ccccc12]
HX259

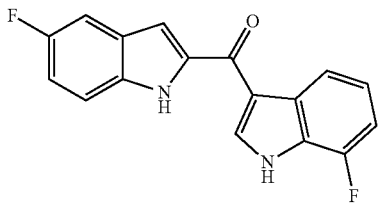 [SMILES: O=C(c1cc2cc(F)ccc2[nH]1)c1c[nH]c2c(F)cccc12]
HX240

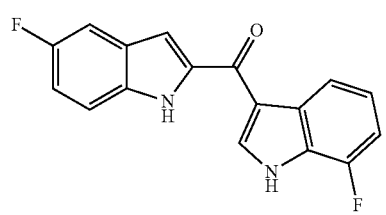
9577

Benzoimidazole indolyl methane ketones (BIIM-ketone):

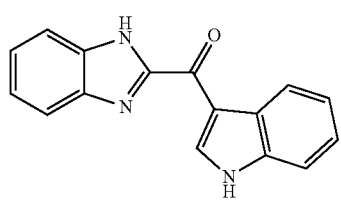
HX262

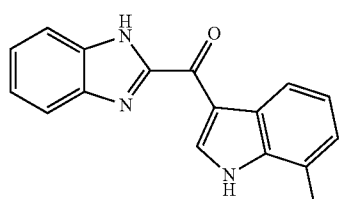
MF025

-continued

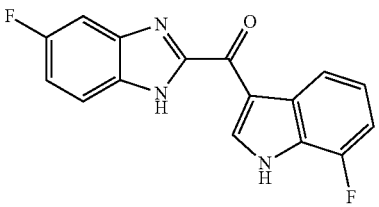
HX235

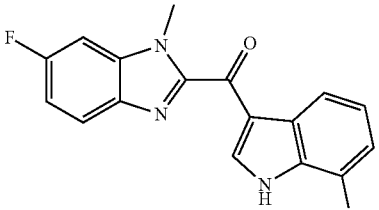
HX261

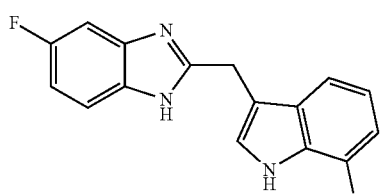
HX81

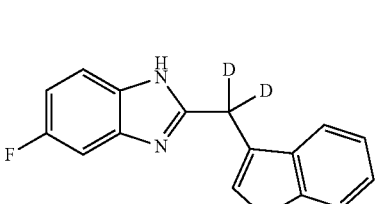
HX212

The activities of these compounds to inhibit PCSK9, using the ELISA described in the Examples is as follows:

TABLE 1

PCSK9-Inhibitory Activity of Select Compounds

| Name | Structure | Activity at 1 μM (% of remaining PCSK9) | Activity at 10 μM (% of remaining PCSK9) |
|---|---|---|---|
| A) Benzoimidazole indolyl methanes (BIIMs) | | | |

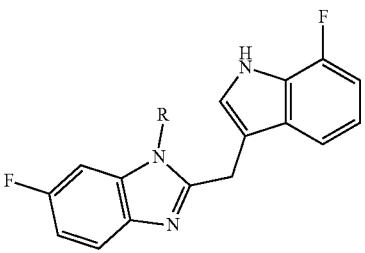

| HX178 | R = Bn | 75% | 31% |
| HX179 | R = CH$_2$CH$_2$Ph | 62% | 48% |

TABLE 1-continued

PCSK9-Inhibitory Activity of Select Compounds

| Name | Structure | Activity at 1 μM (% of remaining PCSK9) | Activity at 10 μM (% of remaining PCSK9) |
| --- | --- | --- | --- |
| HX181 | R = CH$_2$-(4-pyridine) | 60% | 33% |
| HX182 | R = CH$_2$-(3-pyridine) | 86% | 89% |
| HX183 | R = CH$_2$CH$_2$OH | 70% | 27% |
| HX184 | R = CH$_3$ | 34% | 10% |
| HX185 | R = CH$_2$CH(CH$_3$)$_2$ | 65% | 42% |
| HX186 | R = CH$_2$CH(CH$_3$)$_3$ | 84% | 73% |
| HX81 | (structure) | 46% | 14% |
| 9577 | (structure) | 59% | 17% |
| BBR (positive control) | (structure) | 88% | 54% |
| DMSO | | 100% | 100% |

B) Diindolyl methane-ketones (DIIM-ketones)

| Name | Structure | Activity at 1 μM | Activity at 10 μM |
| --- | --- | --- | --- |
| HX257 | (structure) | 25% | 13% |
| HX258 | (structure) | 20% | 14% |

TABLE 1-continued

PCSK9-Inhibitory Activity of Select Compounds

| Name | Structure | Activity at 1 μM (% of remaining PCSK9) | Activity at 10 μM (% of remaining PCSK9) |
|---|---|---|---|
| HX259 | 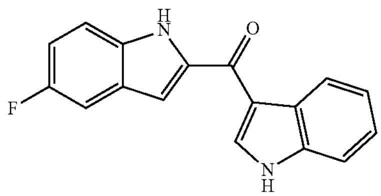 | 28% | 13% |
| HX240 | 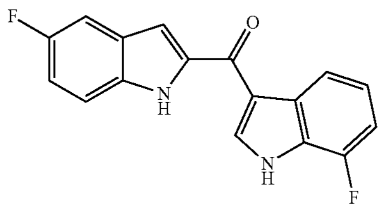 | 25% | 15% |
| 9577 | 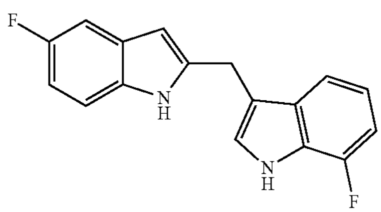 [SMILES: Fc1ccc2[nH]c(Cc3c[nH]c4c(F)cccc34)cc2c1] | 50% | 13% |
| BBR | | 69% | 51% |
| C) Benzoimidazole indolylmethane-ketones (BIIM-ketones) | | | |
| HX262 | 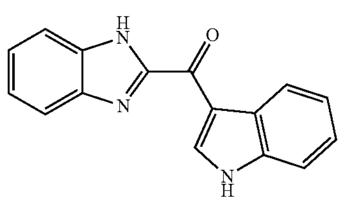 [SMILES: O=C(c1nc2ccccc2[nH]1)c1c[nH]c2ccccc12] | 30% | 20% |
| MF025 | 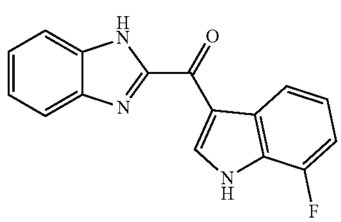 [SMILES: O=C(c1nc2ccccc2[nH]1)c1c[nH]c2c(F)cccc12] | 27% | 21% |
| HX235 | 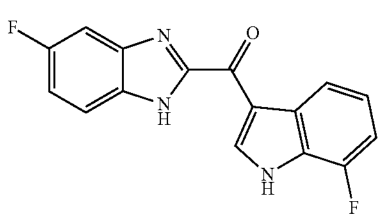 [SMILES: O=C(c1nc2cc(F)ccc2[nH]1)c1c[nH]c2c(F)cccc12] | 28% | 26% |

TABLE 1-continued

PCSK9-Inhibitory Activity of Select Compounds

| Name | Structure | Activity at 1 µM (% of remaining PCSK9) | Activity at 10 µM (% of remaining PCSK9) |
|---|---|---|---|
| HX261 | [structure] | 21% | 20% |
| HX81 | [structure] | 40% | 29% |
| HX212 | [structure] | 45% | 25% |

TABLE 2

|  | 9577 | HX235 | HX240 |
|---|---|---|---|
| $IC_{50}$ (nM) | 44 | 0.5 | 13 |
| $R^2$ | 0.8664 | 0.8738 | 0.9037 |

Nutritional and Pharmaceutical Compositions, Method to Treat Disease States Mediated by PCSK9:

The present disclosure includes nutritional compositions. Such compositions include any food or preparation for human consumption (including for enteral or parenteral consumption) which when taken into the body (a) serve to nourish or build up tissues or supply energy and/or (b) maintain, restore or support adequate nutritional status or metabolic function.

The nutritional composition comprises at least one compound as described herein and may either be in a solid or liquid form. Additionally, the composition may include edible macronutrients, vitamins and minerals in amounts desired for a particular use. The amount of such ingredients will vary depending on whether the composition is intended for use with normal, healthy infants, children or adults having specialized needs such as those which accompany hypercholesterolemic or hyperglipidemic metabolic conditions.

Examples of macronutrients which may be added to the composition include but are not limited to edible fats, carbohydrates and proteins. Examples of such edible fats include but are not limited to coconut oil, soy oil, and mono- and diglycerides. Examples of such carbohydrates include but are not limited to glucose, edible lactose and hydrolyzed search. Additionally, examples of proteins which may be utilized in the nutritional composition include but are not limited to soy proteins, electrodialysed whey, electrodialysed skim milk, milk whey, or the hydrolysates of these proteins.

With respect to vitamins and minerals, the following may be added to the nutritional compositions described herein: calcium, phosphorus, potassium, sodium, chloride, magnesium, manganese, iron, copper, zinc, selenium, iodine, and Vitamins A, E, D, C, and the B complex. Other such vitamins and minerals may also be added.

Examples of nutritional compositions disclosed herein include but are not limited to infant formulas, dietary supplements, dietary substitutes, and rehydration compositions. Nutritional compositions of particular interest include but are not limited to those utilized for enteral and parenteral supplementation for infants, specialist infant formulas, supplements for the elderly, and supplements for those with hyperglycemia.

The nutritional composition of the present invention may also be added to food even when supplementation of the diet is not required. For example, the composition may be added to food of any type including but not limited to margarines, modified butters, cheeses, milk, yoghurt, chocolate, candy, snacks, salad oils, cooking oils, cooking fats, meats, fish and beverages.

In a preferred version, the nutritional composition is an enteral nutritional product, more preferably, an adult or pediatric enteral nutritional product. This composition may be administered to adults or children experiencing stress or having specialized needs due to chronic or acute disease states. The composition may comprise, in addition to compounds and their salts described herein, macronutrients, vitamins and minerals as described above. The macronutrients may be present in amounts equivalent to those present in human milk or on an energy basis, i.e., on a per calorie basis.

Methods for formulating liquid or solid enteral and parenteral nutritional formulas are well known in the art. An enteral formula, for example, may be sterilized and subsequently utilized on a ready-to-feed (RTF) basis or stored in a concentrated liquid or powder. The powder can be prepared by spray drying the formula prepared as indicated above, and reconstituting it by rehydrating the concentrate. Adult and pediatric nutritional formulas are well known in the art and are commercially available (e.g., Similac®-brand and Ensure®-brand formulas from Ross Products Division, Abbott Laboratories, Columbus, Ohio). One or more compounds produced in accordance with the present disclosure may be added to commercial formulas of this type.

The energy density of the nutritional compositions in liquid form may range from about 0.6 Kcal to about 3 Kcal per ml. When in solid or powdered form, the nutritional supplements may contain from about 1.2 to more than 9 Kcals per gram, preferably about 3 to 7 Kcals per gm. In general, the osmolality of a liquid product should be less than 700 mOsm and, more preferably, less than 660 mOsm.

Also disclosed herein are pharmaceutical compositions comprising one or more of the compounds or a pharmaceutically suitable salt thereof as described herein. The pharmaceutical compositions are useful to treat disease states mediated by PCSK9, or exacerbated by PCSK9, including hypercholesterolemia and hyperlipidemia. More specifically, the pharmaceutical composition may comprise one or more of the compounds disclosed herein (and/or a pharmaceutically suitable salt) as well as a standard, well-known, non-toxic pharmaceutically suitable carrier, adjuvant or vehicle such as, for example, phosphate-buffered saline, water, ethanol, polyols, vegetable oils, a wetting agent or an emulsion such as a water/oil emulsion. The composition may be in either a liquid, solid or semi-solid form. For example, the composition may be in the form of a tablet, capsule, ingestible liquid or powder, injectible, suppository, or topical ointment or cream. Proper fluidity can be maintained, for example, by maintaining appropriate particle size in the case of dispersions and by the use of surfactants. It may also be desirable to include isotonic agents, for example, sugars, sodium chloride, and the like. Besides such inert diluents, the composition may also include adjuvants, such as wetting agents, emulsifying and suspending agents, sweetening agents, flavoring agents, perfuming agents, and the like.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art of pharmacy. For example, one or more compounds produced as described herein can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant active ingredient(s) as described herein.

For intravenous administration, the compounds may be incorporated into commercial formulations such as Intralipid©-brand fat emulsions for intravenous injection. ("Intralipid" is a registered trademark of Fresenius Kabi AB, Uppsalla, Sweden.) Where desired, the individual components of the formulations may be provided individually, in kit form, for single or multiple use. A typical intravenous dosage of a representative compound as described herein is from about 0.1 mg to 100 mg daily and is preferably from 0.5 mg to 3.0 mg daily. Dosages above and below these stated ranges are specifically within the scope of the claims.

Possible routes of administration of the pharmaceutical compositions include, for example, enteral (e.g., oral and rectal) and parenteral. For example, a liquid preparation may be administered, for example, orally or rectally. Additionally, a homogenous mixture can be completely dispersed in water (or other suitable vehicle), admixed under sterile conditions with physiologically acceptable diluents, preservatives, buffers or propellants in order to form a spray or inhalant. The route of administration will, of course, depend upon the desired effect and the medical state of the subject being treated. The dosage of the composition to be administered to the patient may be determined by one of ordinary skill in the art and depends upon various factors such as weight of the patient, age of the patient, immune status of the patient, etc., and is ultimately at the discretion of the medical professional administering the treatment.

With respect to form, the composition may be, for example, a solution, a dispersion, a suspension, an emulsion, or a sterile powder which is then reconstituted. The composition may be administered in a single daily dose or multiple doses.

The present disclosure also includes treating hypercholesterolemic and hyperlipidimic disorders in mammals, including humans, by administering an PCSK9-inhibitory-effective amount of one or more the compounds described herein. In particular, the compositions of the present invention may be used to treat hypercholesterolemia and hyperlipidimia of any and all description, but most specifically those that involve a signaling pathway mediated by PCSK9.

The above-described pharmaceutical and nutritional compositions may be utilized in connection with non-human animals, both domestic and non-domestic, as well as humans.

EXAMPLES

The following Examples are included to provide a more complete disclosure of the compounds, compositions, and methods disclosed herein.

Tissue Culture:

The human hepatoma cell line, HepG2, was cultured and maintained in low glucose Dulbecco's modified Eagle's medium (DMEM) supplemented with 10% fetal bovine serum (FBS) and 1% penicillin, streptomycin solution. (ATCC HB-8065, American Type Culture Collection, Manassas, Va.) The medium was further supplemented with 1% each of nonessential amino acids (NEAA), sodium pyruvate and L-glutamine.

Sample Preparation for ELISA of PCSK9 in HepG2:

Freshly cultured HepG2 cells were harvested from vacuum gas plasma-treated T75 cell culture flasks and plated onto vacuum gas plasma-treated clear 12 or 96 well plates (Fisher Scientific, Waltham, Mass. catalog nos. 353072 and 353043, respectively) at 70% confluent in 1000 μl/well or 200 μl/well of growth medium respectively. Cell plates were incubated overnight at 37° C. and 5% $CO_2$ prior to compound treatment. For screening experiments, compounds at an initial concentration of 20 mM in 100% DMSO were diluted to different concentrations in growth medium.

For the generation of dose-response curves, compounds at an initial concentration of 20 mM in 100% DMSO were diluted to 30 μM in growth medium. The 30 μM solutions were then serially diluted 10-fold to achieve final concentration of 30 μM, 3 μM, 0.3 μM, 0.03 μM, and 0.003 μM in assay medium. Growth medium was aspirated from the plated cells and medium containing compound was added to the appropriate well. Cells were allowed to incubate for 24 h or 48 h at 37° C. and 5% $CO_2$. Medium was collected from cells and centrifuged at 14,000 rpm for five min. The upper 50% of spun medium was collected and frozen for later analysis. The remaining cells were washed twice with 1000 μl/well or 200 μl/well cold phosphate buffered saline (PBS) at pH 7.4 and placed on ice. Cells were treated with 100 μl/well or 60 μl/well of lysis buffer comprised of 50 mM Tris, pH 8; 1% NP-40; 150 mM NaCl; 1 mM EDTA (purchased from Cell Signaling Technology, Inc., Danvers, Mass., catalog no. 9803) containing 1 mM phenylmethane sulfonyl fluoride (PMSF) and Roche protease inhibitor cocktail (available from Sigma-Aldrich, St. Louis, Mo.). Cells were allowed to incubate in lysis buffer on ice for 30 min. Cells were then collected and frozen overnight. Cells were centrifuged the next day at 14,000 rpm for 15 min. The supernatant was collected and analyzed for total protein or PCSK9 concentration.

ELISA of PCSK9:

Inhibition of secreted PCSK9 was measured in human hepatocellular carcinoma (HepG2) cells using a PCSK9 Quantikine®-brand ELISA kit purchased from R&D Systems, a wholly owned subsidiary of Bio-Techne Corporation, Minneapolis, Minn. ("Human Proprotein Convertase 9/PCSK9 Quantikine® ELISA Kit," catalog #DPC900). The protocol provided in the kit was followed. Briefly, PCSK9 standards were prepared according to the instructions provided with the kit at final concentrations of 40 ng/mL, 20 ng/mL, 10 ng/mL, 5 ng/mL, 2.5 ng/mL, 1.25 ng/mL, 0.625 ng/mL and 0 ng/mL. The ELISA was conducted with the provided capture antibody-coated 96-well plate. Assay diluent was added to all relevant wells at a volume of 100 μL. 50 μL of sample (medium or cell lysate) or PCSK9 standard (in duplicate) was then added to the appropriate well. The plate was allowed to incubate for 2 h at room temperature. All wells were aspirated and washed four times with 300 μl of wash buffer. After washing, 200 μL of anti-PCSK9-HRP conjugate was added to all wells and the plate was allowed to incubate at room temperature for 2 h. After incubation all wells were aspirated and washed again four times with 300 μL of washing buffer.

After washing was completed, 200 μL of freshly prepared colorimetric reagent was added to all wells and the plate was incubated at room temperature in the dark for 30 min. After this final incubation a stop solution of 1N sulfuric acid was added to all wells, at which point absorbance was measured using a Tecan Infinite M1000 microplate reader at a wavelength of 450 nm (background absorbance was corrected by subtracting the absorbance measured at 540 nm). (Tecan Group Ltd. Mäännedorf, Switzerland.) The data was analyzed with GraphPad Prism 6 software (GraphPad Software, Inc. La Jolla, Calif.) and values were calculated using a four parameter logistic curve fitting equation.

Quantification of Total Protein in Cell Lysate:

Total protein was measured using a Pierce-brand Bicinchoninic Acid (BCA) Protein Assay. The BCA kit was purchased from ThermoFisher Scientific, Waltham, Mass. (catalog #23225). The protocol provided in the kit was followed. Briefly, to a transparent, Corning 96-well plate (Fischer Scientific, catalog no. 3635) was added 10 μl of each provided standard (2000 μg/mL, 1500 μg/mL, 1000 μg/mL, 750 μg/mL, 500 μg/mL, 250 μg/mL, 125 μg/mL, 25 μg/mL, 0 μg/mL) in duplicate. In the appropriate wells, 1 μL or 5 μL of cell lystate sample was added and then diluted with 9 μL or 5 μL of PBS. A "blank" well was prepared by adding 1 μL or 5 μL of lysis buffer to 9 μL or 5 μL of PBS. The BCA reagent was prepared in accordance with the kit instructions. To each well was added 200 μL of freshly prepared BCA reagent, the plate was then sealed and incubated at 37° C. for 30 min. After incubation, absorbance was detected using a Tecan Infinite M1000 microplate reader at an absorbance of 562 nm. The data was analyzed with Graph Pad Prism 6 and values were calculated using a four parameter logistic curve fitting equation.

What is claimed is:

1. A compound having a structure as shown in Formula I:

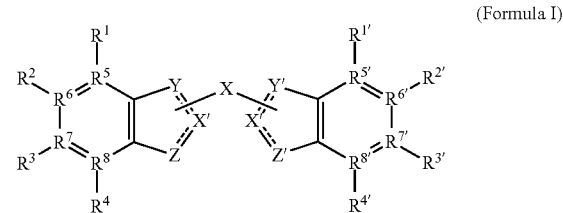

(Formula I)

wherein

X is selected from the group consisting of —$CH_2$—, —$CD_2$—, —$CF_2$—, —CHF—, —CH(OH)—, —C(=O)—, —N(R)—, —S—, —S(=O)—, —S(=O)$_2$—, and cyclopropylene

;

X', Y, Y', Z, and Z' are independently selected from the group consisting of —CH—, —C(R)—, —C(=O)—, —NH—, —N(R)—, —O—, and —S—;

each R is independently selected from the group consisting of hydrogen, halogen, alkyl, and aryl;

$R^1$, $R^2$, $R^3$, $R^4$, $R^{1'}$, $R^{2'}$, $R^{3'}$, and $R^{4'}$ are selected from the group consisting of hydrogen, halogen, alkyl, and aryl, provided that not all of $R^1$, $R^2$, $R^3$, $R^4$, $R^{1'}$, $R^{2'}$, $R^{3'}$, and $R^4$ are simultaneously hydrogen; and $R^2$ and $R^3$ are not methyl when $R^{2'}$ and $R^{3'}$ are hydrogen;

$R^5$, $R^6$, $R^7$, $R^8$, $R^{5'}$, $R^{6'}$, $R^{7'}$ and $R^{8'}$ are independently selected from the group consisting of —C— or —N—, provided that not more than two of $R^5$, $R^6$, $R^7$, $R^8$ and not more than two of $R^{5'}$, $R^{6'}$, $R^{7'}$ and $R^{8'}$ are simultaneously -N—; and salts thereof.

2. The compound of claim 1, having a structure selected from the group consisting of Formula II, III, and IV:

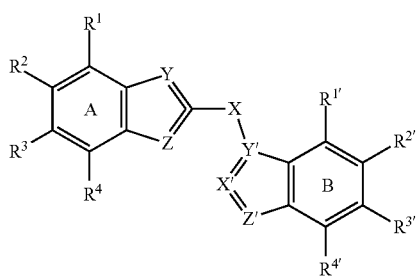

(Formula II)

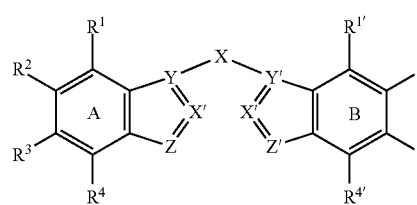

(Formula III)

and

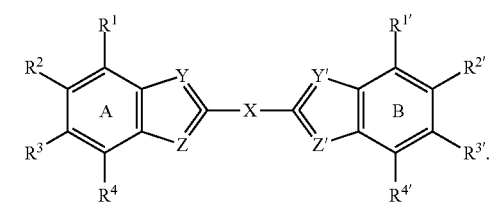

(Formula IV)

3. The compound of claim 2, having a structure as shown in Formula II:

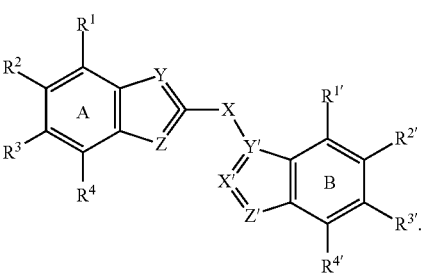

(Formula II)

4. The compound of claim 3, wherein X is selected from the group consisting of —CH$_2$—, —CD$_2$,—, —CF$_2$, —CHF—, —CH(OH)—, and —C(=O)—.

5. The compound of claim 2, having a structure as shown in Formula IV:

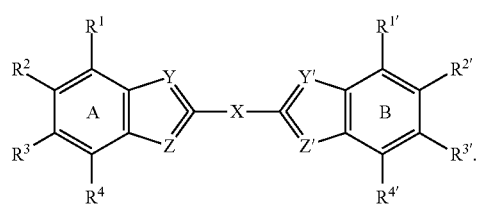

(Formula IV)

6. The compound of claim 5, wherein X is selected from the group consisting of —CH$_2$—, —CD$_2$,—, —CF$_2$, —CHF—, —CH(OH)—, and —C(=O)—.

7. The compound of claim 5, wherein X', Y, Y', Z, and Z' are independently selected from the group consisting of —CH—, —C(R)—, and —C(=O)—.

8. A compound having a structure selected from the group consisting of:

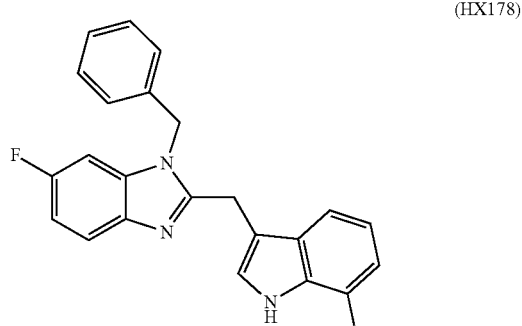

(HX178)

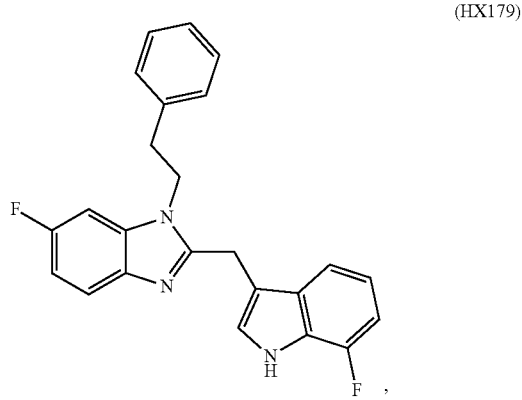

(HX179)

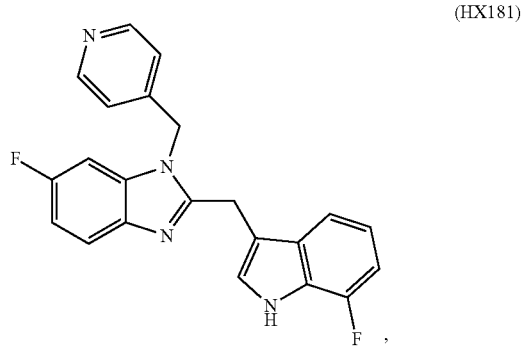

(HX181)

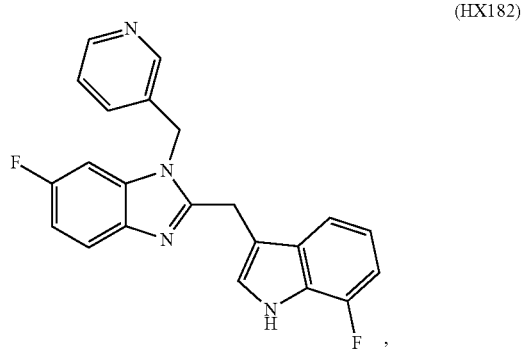

(HX182)

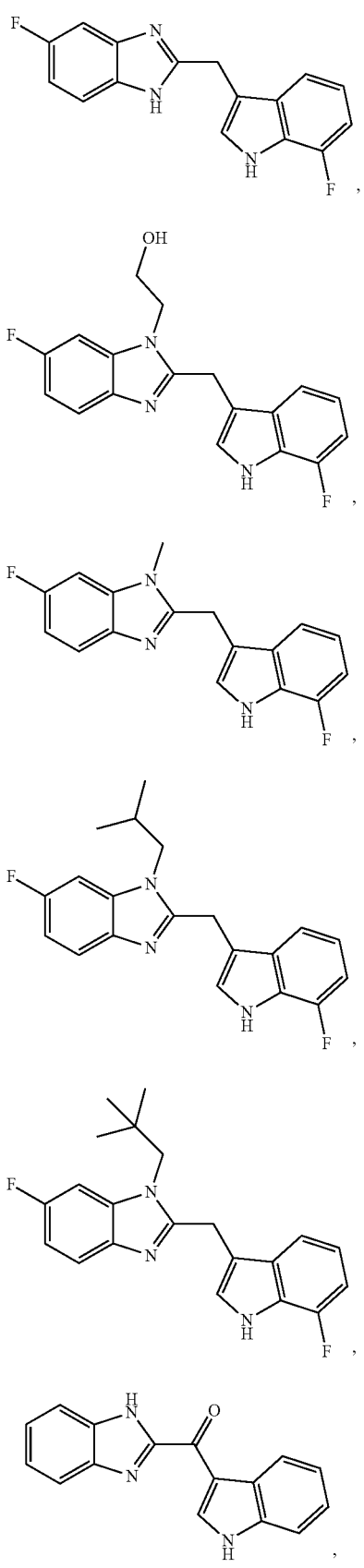
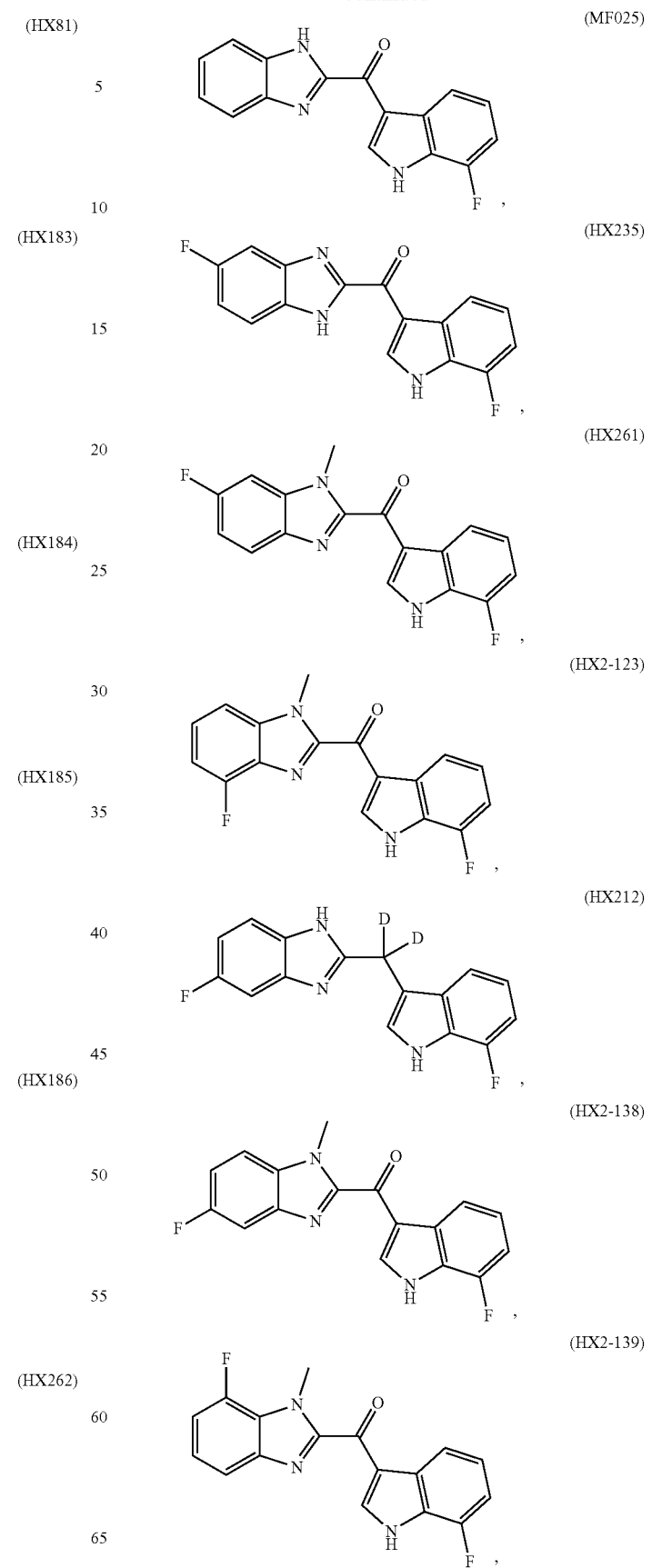

9. A compound having a structure selected from:

[structures HX271 and HX2-080, and additional structures shown]

wherein R is selected from C$_1$-C$_6$— linear or branched alkyl, Ph, -C1—C$_6$-Ph, —C$_1$-C$_6$—(4-pyridine), —C$_1$-C$_6$—(3-pyridine), and —C$_1$-C$_6$—OH.

10. A pharmaceutical composition for ameliorating a PCSK9-mediated ailment, the composition comprising a PCSK9-inhibitory effective amount of a compound having a structure as shown in Formula I:

(Formula I)

wherein
X is selected from the group consisting of —CH$_2$—, —CD$_2$—, —CF$_2$, —CHF—, —CH(OH)—, —C(=O)—, —N(R)—, —S—, —S(=O)—, —S(=O)$_2$—, and cyclopropylene X', Y, Y', Z, and Z' are independently selected from the group consisting of —CH—, —C(R)—, —C(=O)—, —NH—, —N(R)—, —O—, and —S—;

each R is independently selected from the group consisting of hydrogen, halogen, alkyl, and aryl;

$R^1$, $R^2$, $R^3$, $R^4$, $R^{1'}$, $R^{2'}$, $R^{3'}$, and $R^{4'}$ are selected from the group consisting of hydrogen, halogen, alkyl, and aryl, provided that not all of $R^1$, $R^2$, $R^3$, $R^4$, $R^{1'}$, $R^{2'}$, $R^{3'}$, and $R^{4'}$ are simultaneously hydrogen; and $R^2$ and $R^3$ are not methyl when $R^{2'}$ and $R^{3'}$ are hydrogen;

$R^5$, $R^6$, $R^7$, $R^8$, $R^{5'}$, $R^{6'}$, $R^{7'}$ and $R^{8'}$ are independently selected from the group consisting of —C— or —N—, provided that not more than two of $R^5$, $R^6$, $R^7$, $R^8$ and not more than two of $R^{5'}$, $R^{6'}$, $R^{7'}$ and $R^{8'}$ are simultaneously -N—; and pharmaceutically suitable salts thereof;

in combination with a pharmaceutically suitable carrier.

11. A method of inhibiting PCSK9-mediated ailments in mammals, the method comprising administering to a mammal a PCSK9-inhibitory effective amount of a compound having a structure as shown in Formula I:

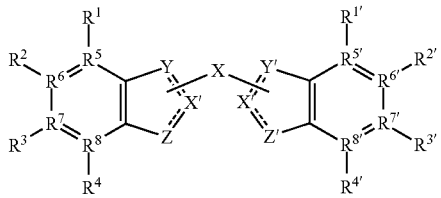

(Formula I)

wherein

X is selected from the group consisting of —CH$_2$—, —CD$_2$—, —CF$_2$, —CHF—, —CH(OH)—, —C(=O)—, —N(R)—, —S—, —S(=O)—, —S(=O)$_2$—, and cyclopropylene

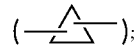

X', Y, Y', Z, and Z' are independently selected from the group consisting of —CH—, —C(R)—, —C(=O)—, —NH—, —N(R)—, —O—, and —S—;

each R is independently selected from the group consisting of hydrogen, halogen, alkyl, and aryl;

$R^1$, $R^2$, $R^3$, $R^4$, $R^{1'}$, $R^{2'}$, $R^{3'}$, and $R^{4'}$ are selected from the group consisting of hydrogen, halogen, alkyl, and aryl, provided that not all of $R^1$, $R^2$, $R^3$, $R^4$, $R^{1'}$, $R^{2'}$, $R^{3'}$, and $R^{4'}$ are simultaneously hydrogen; and $R^2$ and $R^3$ are not methyl when $R^{2'}$ and $R^{3'}$ are hydrogen;

$R^5$, $R^6$, $R^7$, $R^8$, $R^{5'}$, $R^{6'}$, $R^{7'}$ and $R^{8'}$ are independently selected from the group consisting of —C— or —N—, provided that not more than two of $R^5$, $R^6$, $R^7$, $R^8$ and not more than two of $R^{5'}$, $R^{6'}$, $R^{7'}$ and $R^{8'}$ are simultaneously -N—; and salts thereof.

* * * * *

UNITED STATES PATENT AND TRADEMARK OFFICE
CERTIFICATE OF CORRECTION

PATENT NO. : 11,427,569 B2  
APPLICATION NO. : 16/789887  
DATED : August 30, 2022  
INVENTOR(S) : Weiping Tang et al.

Page 1 of 1

It is certified that error appears in the above-identified patent and that said Letters Patent is hereby corrected as shown below:

On the Title Page

Item (54) In the title and in the Specification, Column 1, Lines 1-4, "BENZOIMIDAZOLE INDOLYL METHANES AND METHODS OF USING THEM TO INHIBIT PCKS9 AND PCKS9-MEDIATED AILMENTS" should read "BENZOIMIDAZOLE INDOLYL METHANES AND METHODS OF USING THEM TO INHIBIT PCSK9 AND PCSK9-MEDIATED AILMENTS".

Signed and Sealed this  
Twenty-eighth Day of March, 2023

Katherine Kelly Vidal  
*Director of the United States Patent and Trademark Office*